(12) United States Patent
Baceiredo et al.

(10) Patent No.: US 9,624,251 B2
(45) Date of Patent: Apr. 18, 2017

(54) CATALYSTS HAVING A SILENE LIGAND

(71) Applicants: BLUESTAR SILICONES FRANCE SAS, Lyons (FR); CENTRE NATIONAL DE LA RECHERCHE SCIENTIFIQUE-CNRS-, Paris (FR)

(72) Inventors: Antoine Baceiredo, Toulouse (FR); Tsuyoshi Kato, Toulouse (FR); Ricardo Rodriguez, Tauste (ES); Norio Nakata, Saitama (JP); Sébastien Marrot, Lyons (FR); Laurent Saint-Jalmes, Vourles (FR)

(73) Assignees: BLUESTAR SILICONES FRANCE SAS, Lyons (FR); CENTRE NATIONAL DE LA RECHERCHE SCIENTIFIQUE—CNRS, Paris (FR)

( * ) Notice: Subject to any disclaimer, the term of this patent is extended or adjusted under 35 U.S.C. 154(b) by 40 days.

(21) Appl. No.: 14/903,224

(22) PCT Filed: Jul. 11, 2014

(86) PCT No.: PCT/FR2014/051788
§ 371 (c)(1),
(2) Date: Jan. 6, 2016

(87) PCT Pub. No.: WO2015/004397
PCT Pub. Date: Jan. 15, 2015

(65) Prior Publication Data
US 2016/0145283 A1 May 26, 2016

(30) Foreign Application Priority Data
Jul. 12, 2013 (FR) ...................................... 13 56886

(51) Int. Cl.
| *C07F 19/00* | (2006.01) |
| *C07F 15/00* | (2006.01) |
| *B01J 31/00* | (2006.01) |
| *B01J 31/16* | (2006.01) |
| *B01J 31/22* | (2006.01) |
| *C07F 7/08*  | (2006.01) |

(52) U.S. Cl.
CPC ....... *C07F 15/0086* (2013.01); *B01J 31/1608* (2013.01); *B01J 31/2291* (2013.01); *C07F 7/0829* (2013.01); *C07F 7/0879* (2013.01); *B01J 2231/323* (2013.01); *B01J 2531/828* (2013.01)

(58) Field of Classification Search
CPC .. C07F 15/0086; C07F 7/0879; C07F 7/0829; B01J 31/1608; B01J 31/2291
USPC ................ 556/12, 20, 479; 568/12; 502/155
See application file for complete search history.

(56) References Cited

U.S. PATENT DOCUMENTS

| 2003/0083454 A1 | 5/2003 | Narko et al. |
| 2009/0182091 A1 | 7/2009 | Noro et al. |
| 2009/0182099 A1 | 7/2009 | Noro et al. |

FOREIGN PATENT DOCUMENTS

| FR | 1 528 464 A   | 6/1968 |
| FR | 2 372 874 A1  | 6/1978 |
| WO | 01/42258 A1   | 6/2001 |

OTHER PUBLICATIONS

Dec. 8, 2014 Search Report issued in International Patent Application No. PCT/FR2014/051788.
Bravo-Zhivotovskii, Dmitry et al., "The Direct Synthesis of a Silene-Organometallic Complex", Angewandte Chemie International Edition, Jan. 30, 2004, vol. 43, No. 6, XP055107863, pp. 745-748.
Nakata, Norio et al., "A Stable Silene Substituted by Strong π-Donors at the Silicon Center", Angewandte Chemie, International Edition, 52(41), 10840-10844 Coden: ACIEF5, ISSN: 1433-7851, 2013, XP002732549.

*Primary Examiner* — Porfirio Nazario Gonzalez
(74) *Attorney, Agent, or Firm* — Oliff PLC

(57) ABSTRACT

A subject matter of the present invention is the use as catalyst, in particular in hydrosilylation, of a metal complex including at least one metal atom chosen from the metals of Groups 8, 9 and 10 of the Periodic Table of the Elements and one or more ligands, characterized in that at least one ligand includes a silene structure.

9 Claims, No Drawings

CATALYSTS HAVING A SILENE LIGAND

FIELD OF THE INVENTION

The invention relates to the use of metal complexes of a novel type as catalysts, in particular as hydrosilylation catalysts. More specifically, the present invention relates to the use of metal complexes having at least one ligand of silene type.

PRIOR ART

During a hydrosilylation (also known as polyaddition) reaction, a compound comprising at least one unsaturation reacts with a compound comprising at least one hydrosilyl functional group, that is to say a hydrogen atom bonded to a silicon atom. This reaction can, for example, be described, in the case of an unsaturation of alkene type, by:

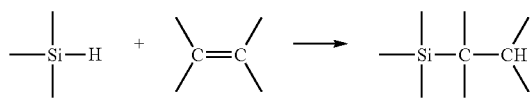

or, in the case of an unsaturation of alkyne type, by:

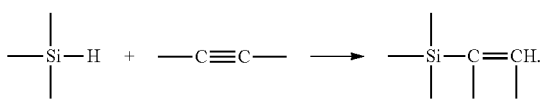

The hydrosilylation of unsaturated compounds is carried out by catalysis. Typically, the appropriate catalyst for this reaction is a platinum catalyst. Currently, the majority of industrial hydrosilylation reactions are catalyzed by the Karstedt platinum complex, of general formula $Pt_2$(divinyltetramethyldisiloxane)$_3$ (or in abbreviation $Pt_2(DVTMS)_3$):

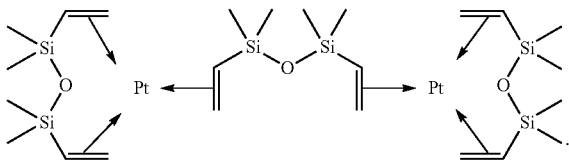

At the beginning of the 2000s, the preparation of platinum-carbene complexes of general formula:

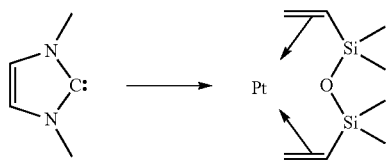

made it possible to access more stable catalysts (see, for example, the international patent application WO 01/42258).

However, the use of platinum catalysts is still problematic. It concerns an expensive metal, which is becoming scarcer, and the cost of which fluctuates enormously. Its use on an industrial scale is difficult. It is thus desirable to reduce as much as possible the amount of catalyst necessary for the reaction, without, however, reducing the yield and the speed of the reaction.

Furthermore, it is desirable to have available a catalyst which is stable during the reaction. It has been found that, during the catalyzed reaction, platinum metal could precipitate, which has the consequence of the formation of colloids which are insoluble in the reaction medium. The catalyst is then less active. Furthermore, these colloids form a haze in the reaction medium and the products obtained are not esthetically satisfactory as they are colored.

In addition, during hydrosilylation reactions with the Karstedt catalyst, the formation has been observed of undesirable byproducts resulting from the isomerization of an olefinic double bond and/or from hydrogenation reactions. It is also desirable for the catalyst not to promote side reactions.

In this context, one of the objectives of the present invention is to provide a novel type of catalyst suitable in particular for the catalysis of hydrosilylation reactions. Advantageously, this catalyst can be used in a smaller amount than the existing catalysts, while retaining at least the same effectiveness. In addition, the novel catalyst can advantageously be stable in the reaction medium, not form colloids and make it possible to limit side reactions.

BRIEF DESCRIPTION OF THE INVENTION

These objectives have been achieved by virtue of the employment of a novel type of catalyst. A subject matter of the present invention is the use as catalyst of a metal complex comprising at least one metal atom chosen from the metals of Groups 8, 9 and 10 of the Periodic Table of the Elements and one or more ligands, characterized in that at least one ligand comprises a silene structure.

In addition, another subject matter of the invention is, on the one hand, a process for the hydrosilylation of an unsaturated compound comprising at least one alkene functional group and/or at least one alkyne functional group with a compound comprising at least one hydrosilyl functional group, said process being characterized in that it is catalyzed by a metal complex comprising at least one metal atom chosen from the metals of Groups 8, 9 and 10 of the Periodic Table of the Elements and one or more ligands, characterized in that at least one ligand comprises a silene structure, and, on the other hand, a composition comprising:
- at least one unsaturated compound comprising at least one alkene functional group and/or at least one alkyne functional group,
- at least one compound comprising at least one hydrosilyl functional group, and
- a catalyst chosen from the metal complexes comprising at least one metal atom chosen from the metals of Groups 8, 9 and 10 of the Periodic Table of the Elements and one or more ligands, characterized in that at least one ligand comprises a silene structure.

Finally, a metal complex comprising at least one metal atom chosen from the metals of Groups 8, 9 and 10 of the Periodic Table of the Elements and one or more ligands, characterized in that at least one ligand comprises a silene-phosphorus ylide structure, is also a subject matter of the present invention.

DETAILED DESCRIPTION OF THE INVENTION

According to a first aspect, the present invention thus relates to a specific use of certain metal complexes. These metal complexes are characterized in that they comprise at least one metal atom chosen from the metals of Groups 8, 9 and 10 of the Periodic Table of the Elements and one or more ligands, at least one ligand comprising a silene structure.

These metal complexes can be represented by the general formula (I):

$$[M_a(Lig)_b]^c \qquad (I)$$

in which:

M represents a metal chosen from the metals of Groups 8, 9 and 10 of the Periodic Table of the Elements;

the symbol Lig represents a ligand of the metal M;

a is 1, 2 or 3;

b is an integer ranging from 1 to a number equal to 5 times the value of a;

c corresponds to the total charge of the metal complex, which can be 0 or a positive integer ranging from +1 to +6;

it being understood that, if b is greater than or equal to 2, Lig can represent identical or different ligands, characterized in that at least one ligand Lig is a ligand which comprises a silene structure.

In the present invention, the metals of Groups 8, 9 and 10 of the Periodic Table of the Elements are iron (Fe), ruthenium (Ru), osmium (Os), hassium (Hs), cobalt (Co), rhodium (Rh), iridium (Ir), meitnerium (Mt), nickel (Ni), palladium (Pd), platinum (Pt) and darmstadtium (Ds). Preferably, the metal of the metal complex according to the invention is chosen from the group consisting of Pt, Pd, Ni, Rh, Ru, Os and Ir, more preferably from the group consisting of Pt, Pd, Ni, Rh and Ru, and even more preferably from the group consisting of Pt, Pd and Ru. Very preferably, the metal is Pt and the metal complex of the present invention is a platinum complex.

The complex can comprise just one metal atom, which means that the symbol "a" has the value 1 in the general formula (I). However, it is also possible for the metal complex to comprise several metal atoms, in particular if at least one of the ligands of the complex is a bridging ligand or a polydentate ligand.

The metal complex according to the invention can be neutral (which means that the symbol "c" has the value 0 in the general formula (I)) or else charged (the symbol "c" in the general formula (I) is other than 0 and has the value +1, +2, +3, +4, +5 or +6). In the latter case, the metal complex can be associated with one or more counterions.

One or more ligands will complex the metal atom or atoms. The metal complex according to the invention is characterized in that at least one ligand comprises a silene structure. In the continuation, this ligand is denoted "$L_S$".

A silene compound is a chemical compound comprising a silicon atom and a carbon atom bonded via a double bond:

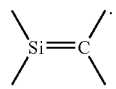

The synthesis of the first compounds comprising a silicon-carbon double bond goes back to the start of the 1980s. These compounds have since formed the subject of numerous studies but it was only in the 1990s that metal complexes having a ligand of silene type were described for the first time. The nature of the interactions between the metal atom and the ligand of silene type is studied, for example, in the paper by Bravo-Zhivotovskii et al.: "The Direct Synthesis of a Silene-Organometallic Complex", *Agnew. Chem. Int. Ed.*, 2004, 43, 745-748. It emerges from this publication that a metal complex with a ligand of silene type can be regarded as a complex of it type or as a compound of cyclopropane type bonded via bonds of a type. However, in that which follows, the complexing between ligand $L_S$ and a metal atom M will be represented diagrammatically by:

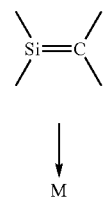

To the knowledge of the inventors, no application in catalysis of a metal complex with a ligand of silene type has been described.

Among the ligands comprising a silene structure, $L_S$ can be a compound of formula (II):

in which each $R^a$ is independently chosen from:

a hydrogen atom, a halogen atom, an alkyl group, optionally substituted one or more times by a halogen atom, by a haloalkyl group, by a cycloalkyl group, by a cycloalkylalkyl group, by an aryl group, by an arylalkyl group, by an acyl group, by an amine group, by an hydroxyl group or by an alkoxy group, a cycloalkyl group, optionally substituted one or more times by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group, a cycloalkylalkyl group, optionally substituted one or more times on the cycloalkyl part and/or on the alkyl part by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group, an aryl group, optionally substituted one or more times by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group, an arylalkyl group, optionally substituted one or more times on the aryl part and/or on the alkyl part by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group, an acyl group, optionally substituted one or more times by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group, an hydroxyl group, an alkoxy group, optionally substituted one or more times on the alkyl part by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group, an amine, imine or amide group, optionally substituted one or more times by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group, and a phosphine, phosphite, phosphorane or phosphorus ylide group, optionally substituted one or more times by a halogen atom, by an alkyl group, by a cycloalkyl group, by a cycloalkylalkyl group, by an aryl group, by an arylalkyl group, by an acyl group, by an amine group, by an hydroxyl group or by an alkoxy group;

it being understood that:

in each $R^a$ group, one or more carbon atoms can be replaced with a silicon Si atom, in each $R^a$ group, one or more unsaturations may be present, two groups or more chosen from the $R^a$ groups, with the atoms to which they are bonded, can form a monocyclic or polycyclic ring, consisting of 3 to 20 ring members, optionally comprising one or more unsaturations and optionally comprising one or more heteroatoms chosen from 0, N, Si and P, it being possible for the monocyclic or polycyclic ring group to be optionally substituted one or more times by a halogen atom, by an alkyl group, by a cycloalkyl group, by a cycloalkylalkyl group, by an aryl group, by an arylalkyl group, by an acyl group, by an amine group, by an hydroxyl group or by an alkoxy group.

The term "halogen atom" is understood to mean, according to the invention, an atom chosen from the group consisting of fluorine, chlorine, bromine and iodine.

The term "alkyl" is understood to mean, according to the invention, a saturated, linear or branched, hydrocarbon chain comprising from 1 to 20 carbon atoms, preferably from 1 to 8 carbon atoms. An alkyl group can be chosen from the group consisting of methyl, ethyl, isopropyl, n-propyl, tert-butyl, isobutyl, n-butyl, n-pentyl, isoamyl and 1,1-dimethylpropyl.

The term "cycloalkyl" is understood to mean, according to the invention, a saturated, monocyclic or polycyclic, preferably monocyclic or bicyclic, hydrocarbon group containing from 3 to 20 carbon atoms, preferably from 3 to 8 carbon atoms. When the cycloalkyl group is polycyclic, the multiple cyclic nuclei can be attached to one another via a covalent bond and/or via a spiran atom and/or be condensed with one another. A cycloalkyl group can be chosen from the group consisting of cyclopropyl, cyclobutyl, cyclopentyl, cyclohexyl, cycloheptyl, cyclooctyl, adamantyl and norbornyl.

The term "cycloalkylalkyl" is understood to mean, according to the invention, an alkyl group as defined above substituted by a cycloalkyl group, also as defined above.

The term "aryl" is understood to mean, according to the invention, an aromatic, monocyclic or polycyclic, hydrocarbon group containing from 5 to 18 carbon atoms. An aryl group can be chosen from the group consisting of phenyl, naphthyl, anthracenyl and phenanthryl.

The term "arylalkyl" is understood to mean, according to the invention, an alkyl group as defined above substituted by a cycloalkyl group, also as defined above.

The term "acyl" is understood to mean, according to the invention, an alkyl, cycloalkyl or aryl group as defined above bonded to a C=O group.

The term "alkoxy" is understood to mean, according to the invention, an alkyl group as defined above bonded to an oxygen atom. An alkoxy group can be chosen from the group consisting of methoxy, ethoxy, propoxy and butoxy.

The term "amine" is understood to mean, according to the invention, a primary amine group or else a secondary, tertiary or quaternary amine group, the substituent or substituents of which are chosen from an alkyl group as defined above.

More specifically, $L_S$ can be a compound of formula (III):

(III)

in which each $R^a$ is as defined above,
and each $R^{a'}$ can be independently chosen from:
a hydrogen atom,
a halogen atom,
a $C_1$ to $C_6$ alkyl group, optionally substituted one or more times by a halogen atom,
a $C_1$ to $C_6$ cycloalkyl group, optionally substituted one or more times by a halogen atom,
a $C_1$ to $C_6$ aryl group, optionally substituted one or more times by a halogen atom, or else the two $R^{a'}$ groups, with the carbon atom to which they are bonded, can form a monocyclic ring, composed of 3 to 6 ring members, optionally comprising one or more unsaturations and optionally comprising one or more heteroatoms chosen from O, N, Si and P, it being possible for the monocyclic or polycyclic ring group to be optionally substituted one or more times by a halogen atom.

According to a preferred embodiment, the silene structure of the ligand is a silene-phosphorus ylide.

The term "silene-phosphorus ylide" is understood to mean a compound consecutively comprising a silene group

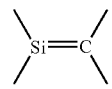

and a phosphorus ylide group

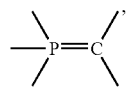

the carbon atom of the phosphorus ylide group being bonded to the silicon atom of the silene group. Thus, a silene-phosphorus ylide structure can be represented diagrammatically by:

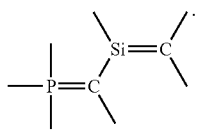

To the knowledge of the inventors, no metal complex having a compound of silene-phosphorus ylide structure as ligand has been described previously. This is why the metal complexes comprising at least one metal atom chosen from the metals of Groups 8, 9 and 10 of the Periodic Table of the Elements and one or more ligands, characterized in that at least one ligand comprises a silene-phosphorus ylide structure, are also a subject matter of the present invention. This metal complex which is the subject matter of the invention can preferably be as described below in the context of its use as catalyst.

More specifically, the ligand $L_S$ can be a compound of formula (IV):

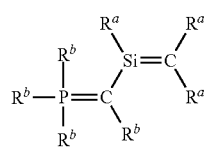

(IV)

in which each $R^a$ is as defined above,
and each $R^b$ can be independently chosen from:
a hydrogen atom,
a halogen atom,
an alkyl group, optionally substituted one or more times by a halogen atom, by a haloalkyl group, by a cycloalkyl group, by a cycloalkylalkyl group, by an aryl group, by an arylalkyl group, by an acyl group, by an amine group, by an hydroxyl group or by an alkoxy group,
a cycloalkyl group, optionally substituted one or more times by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group,
a cycloalkylalkyl group, optionally substituted one or more times on the cycloalkyl part and/or on the alkyl part by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group,
an aryl group, optionally substituted one or more times by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group,
an arylalkyl group, optionally substituted one or more times on the aryl part and/or on the alkyl part by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group,
an acyl group, optionally substituted one or more times by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group,
an hydroxyl group,
an alkoxy group, optionally substituted one or more times on the alkyl part by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group,
an amine, imine or amide group, optionally substituted one or more times by a halogen atom, by an alkyl group, by a haloalkyl group, by a cycloalkyl group, by a cycloalkylalkyl group, by an aryl group, by an arylalkyl group, by an acyl group, by an amine group, by an hydroxyl group or by an alkoxy group, and
a phosphine, phosphite, phosphorane or phosphorus ylide group, optionally substituted one or more times by a halogen atom, by an alkyl group, by a cycloalkyl group, by a cycloalkylalkyl group, by an aryl group, by an arylalkyl group, by an acyl group, by an amine group, by an hydroxyl group or by an alkoxy group;
it being understood that:
in each $R^b$ group, one or more carbon atoms can be replaced with a silicon Si atom,
in each $R^b$ group, one or more unsaturations may be present,
two groups or more chosen from the $R^a$ groups and the $R^b$ groups, with the atoms to which they are bonded, can form a monocyclic or polycyclic ring, consisting of 3 to 20 ring members, optionally comprising one or more unsaturations and optionally comprising one or more heteroatoms chosen from O, N, Si and P, it being possible for the monocyclic or polycyclic ring group to be optionally substituted one or more times by a halogen atom, by an alkyl group, by a cycloalkyl group, by a cycloalkylalkyl group, by an aryl group, by an arylalkyl group, by an acyl group, by an amine group, by an hydroxyl group or by an alkoxy group.

The ligand $L_S$ can in particular be a compound of formula (V):

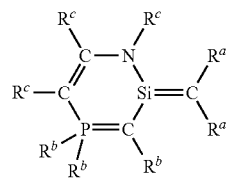

(V)

in which each $R^a$ and each $R^b$ are as defined above,
and each $R^e$ can be independently chosen from:
a hydrogen atom,
a halogen atom,
an alkyl group,
a cycloalkyl group,
a cycloalkylalkyl group,
an aryl group,
an arylalkyl group,
an acyl group,
an amine group,
a hydroxyl group, by an alkoxy group,
it being understood that:
in each $R^c$ group, one or more carbon atoms can be replaced with a silicon Si atom,
in each $R^c$ group, one or more unsaturations may be present,
two groups or more chosen from the $R^a$ groups, the $R^b$ groups and the $R^c$ groups, with the atoms to which they are bonded, can form a monocyclic or polycyclic ring, consisting of 3 to 20 ring members, optionally comprising one or more unsaturations and optionally comprising one or more heteroatoms chosen from O, N, Si and P, it being possible for the monocyclic or polycyclic ring group to be optionally substituted one or more times by a halogen atom, by an alkyl group, by a cycloalkyl group, by a cycloalkylalkyl group, by an aryl group, by an arylalkyl group, by an acyl group, by an amine group, by an hydroxyl group or by an alkoxy group.

Very particularly, the ligand $L_S$ can be the compound of formula (VI):

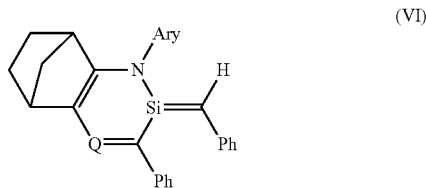

(VI)

in which the symbol "Q" represents

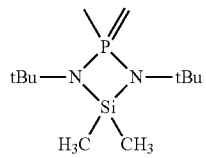

and
the symbol "Ary" represents

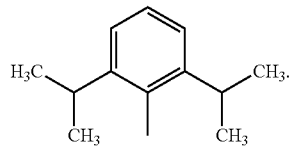

In all cases, if the ligand $L_S$ contains asymmetrical atoms (in particular carbon, nitrogen or phosphorus atoms), $L_S$ can be a pure isomer, for example an enantiomer or a diastereomer, or a mixture of isomers, in particular a racemic mixture. It can be particularly advantageous to have available the ligand $L_S$ in the form of a pure isomer as the metal complexes comprising this ligand may have advantageous properties in asymmetric synthesis and catalysis.

The ligand $L_S$, which comprises a silene structure, can be prepared according to the methods conventionally used to prepare silene compounds, in particular by a thermal route, by a photochemical route or by 1,2-elimination.

Mention may be made, among the thermal routes which can conventionally be employed, of retro-Diels-Alder reactions.

Among the photochemical routes, one synthetic route known in the literature consists in reacting a lithiated disilane with a ketone. The reaction medium is subjected to irradiation, which results in the formation of a silene compound. This reaction can be represented diagrammatically by:

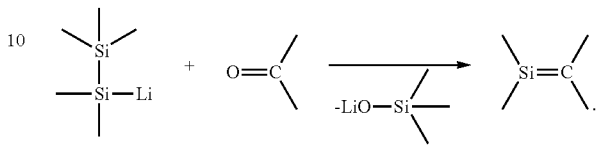

A silene compound can also be obtained by a photochemical route by subjecting a disilane compound having a diazo group in the alpha position to irradiation. The departure of a nitrogen molecule is accompanied by a rearrangement which results in the formation of a silene compound. This reaction can be represented diagrammatically by:

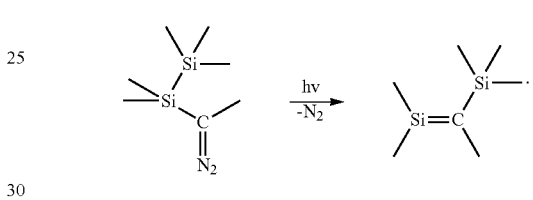

Finally, the ligand $L_S$ can also be prepared by 1,2-elimination starting from a halosilane precursor comprising, in the α position with respect to the silicon, a halogen atom or an unsaturation. A strong base, such as an organolithium compound, can be used as reactant. This reaction can be represented diagrammatically by:

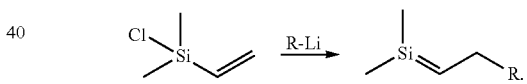

Alternately, the ligand $L_S$ can be prepared by any other method of synthesis available in the literature which makes possible the synthesis of a silene compound.

Furthermore, when the ligand $L_S$ according to a preferred embodiment of the invention is a silene-phosphorus ylide, the phosphorus ylide group can be prepared by any method of synthesis known to a person skilled in the art. Typically, the phosphorus ylides are prepared by deprotonation of a phosphonium salt using, for example, a strong base, such as an organolithium compound. The silene and phosphorus ylide groups can be obtained in a single stage, in concerted fashion, or in several stages.

The metal complex, the use of which is a subject matter of the present invention, comprises at least one metal atom chosen from the metals of Groups 8, 9 and 10 of the Periodic Table of the Elements and at least one ligand $L_S$ as defined above. The metal complex can comprise just one ligand $L_S$ or several ligands $L_S$. If several ligands $L_S$ are present, these can be identical or different. In addition, the metal complex can comprise one or more other ligands. The number and the nature of the ligands are appropriate for the valency of the metal atom.

Preferably, the metal complex according to the invention comprises one or more other ligands chosen, independently of one another, from the group consisting of carbon monoxide, phosphines, amines, molecular hydrogen, halogens, carboxylate ions, sulfonate ions, amide radicals, alkoxide radicals, acetylacetonate radicals, alkyl radicals having from 1 to 7 carbon atoms, nitrogen monoxide, nitriles, isonitriles, mono- and diolefins, alkynes and aromatic radicals. The ligand can be monodentate or polydentate, in particular bidentate, tridentate or quadridentate.

The metal complex according to the invention can comprise, as ligand, divinyltetramethyldisiloxane (DVTMS), of formula:

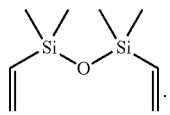

According to a quite specific embodiment, the metal complex is the compound of formula (VII):

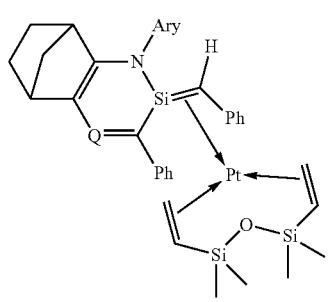

(VII)

in which the symbol "Q" represents

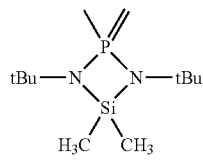

and
the symbol "Ary" represents

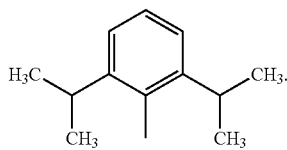

The metal complexes according to the invention can be prepared from known complexes of the state of the art by ligand exchange, that is to say by addition of at least one ligand $L_S$ to an appropriate precursor metal complex, in solution. The precursor metal complex can in particular be chosen from metal complexes having a divinyl ligand, metal complexes having a cyclooctadiene ligand and metal complexes having an olefin and bisphosphine ligand. Preferably, the precursor metal complex is chosen from metal complexes of formula $M(COD)_2$ and metal complexes of formula $M_2(DVTMS)_3$, "M" representing a metal of Groups 8, 9 and 10 of the Periodic Table of the Elements, "COD" representing the cycloocta-1,5-diene ligand and "DVTMS" representing the 1,3-divinyl-1,1,3,3-tetramethyldisiloxane ligand. Very preferably, the precursor metal complex is the Karstedt platinum complex $Pt_2(DVTMS)_3$.

The use of these metal complexes as catalyst is a subject matter of the present invention. In particular, they can be catalysts for reactions known to a person skilled in the art as being able to be catalyzed by organometallic catalysts having ligands of carbene type. The inventors have found that, entirely unexpectedly, the metal complexes according to the invention make it possible to catalyze reactions, such as hydrosilylation, as effectively as and sometimes even more effectively than the catalysts conventionally used, such as the Karstedt catalyst, while employing a smaller amount of catalyst. This result is particularly advantageous as it makes it possible to reduce the concentration of catalyst, and thus of platinum, in the reaction medium without affecting the yield of the reaction. Furthermore, during the use of these catalysts, the formation of colloids was not observed and the formation of byproducts was not promoted, indeed even was reduced, with respect to that obtained with the catalyst conventionally used, such as the Karstedt catalyst.

The present invention can also relate to a catalyst comprising at least one metal complex as described above and to a method for carrying out a chemical reaction, characterized in that the reaction is catalyzed by one of these metal complexes.

Among the different reactions which can be catalyzed by the metal complex described here, a subject matter of the invention is very particularly a process for the hydrosilylation of an unsaturated compound comprising at least one alkene functional group and/or at least one alkyne functional group with a compound comprising at least one hydrosilyl (≡Si—H) functional group, said process being characterized in that it is catalyzed by a metal complex as defined above. In this process, the metal complex is preferably a platinum complex.

According to a first embodiment, the compound comprising at least one hydrosilyl functional group is a silane or polysilane compound comprising at least one hydrogen atom bonded to a silicon atom. "Silane" compound is understood to mean, in the present invention, the chemical compounds comprising a silicon atom bonded to four hydrogen atoms or to organic substituents. "Polysilane" compound is understood to mean, in the present invention, the chemical compounds having at least one unit.

According to a second embodiment, the compound comprising at least one hydrosilyl functional group is a siloxane compound comprising at least one hydrogen atom bonded to a silicon atom. "Siloxane" compound is understood to mean, in the present invention, chemical compounds having at least one unit. The siloxane compound comprises at least two silicon atoms, preferably at least 3 silicon atoms or more. Said siloxane compound can advantageously be a polyorganosiloxane (commonly denoted POS) comprising at least one unit of formula (VIII):

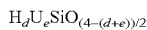 (VIII)

in which:
U represents a monovalent radical other than a hydrogen atom,
d and e represent integers, d having the value 1 or 2, e the value 0, 1 or 2 and (d+e) having the value 1, 2 or 3;
and optionally other units of formula (IX):

 (IX)

in which U has the same meaning as above and f represents an integer of between 0 and 3. It is understood, in the formula (VIII) and in the formula (IX) above, that, if several U groups are present, they can be identical to or different from one another.

In the formula (VIII), the symbol d can preferably have the value 1.

Furthermore, in the formula (VIII) and in the formula (IX), U can represent a monovalent radical chosen from the group consisting of an alkyl group having from 1 to 8 carbon atoms, optionally substituted by at least one halogen atom, and an aryl group. U can advantageously represent a monovalent radical chosen from the group consisting of methyl, ethyl, propyl, 3,3,3-trifluoropropyl, xylyl, tolyl and phenyl. Examples of units of formula (VIII) are as follows: $H(CH_3)_2SiO_{1/2}$, $HCH_3SiO_{2/2}$ and $H(C_6H_5)SiO_{2/2}$.

The polyorganosiloxane can exhibit a linear, branched, cyclic or network structure.

Examples of polyorganosiloxanes which can be siloxane compounds comprising at least one hydrogen atom bonded to a silicon atom are:
  a poly(dimethylsiloxane) having hydrodimethylsilyl ends;
  a poly(dimethylsiloxane-co-methylhydrosiloxane) having trimethylsilyl ends;
  a poly(dimethylsiloxane-co-methylhydrosiloxane) having hydrodimethylsilyl ends;
  a poly(methylhydrosiloxane) having trimethylsilyl ends; and
  a cyclic poly(methylhydrosiloxane).

Preferably, the compound comprising at least one hydrosilyl functional group is a polyorganosiloxane compound comprising, per molecule, at least two hydrosilyl (Si—H) functional groups.

Finally, according to a third embodiment, the compound comprising at least one hydrosilyl functional group is an organic polymer comprising hydrosilyl functional groups at the terminal positions. The organic polymer can, for example, be a polyoxyalkylene, a saturated hydrocarbon polymer or a poly(meth)acrylate. Organic polymers comprising reactive functional groups at the terminal positions are described in particular in patent applications US 2009/0182099 and US 2009/0182091.

The second of the reactants of the hydrosilylation reaction is an unsaturated compound. The unsaturated compound according to the invention is a chemical compound comprising at least one unsaturation not forming part of an aromatic ring. The unsaturated compound comprises at least one alkene functional group and/or one alkyne functional group. Any compound comprising at least one alkene functional group and/or one alkyne functional group can be used in the process according to the invention, insofar as it does not comprise a reactive chemical functional group which can hinder, and even prevent, the hydrosilylation reaction.

According to one embodiment, the unsaturated compound comprises one or more alkene functional groups and from 2 to 40 carbon atoms. According to another embodiment, the unsaturated compound comprises one or more alkyne functional groups and from 2 to 40 carbon atoms.

The unsaturated compound can preferably be chosen from the group consisting of acetylene, $C_1$ to $C_4$ alkyl acrylates and methacrylates, acrylic acid or methacrylic acid, alkenes, preferably octene and more preferably 1-octene, allyl alcohol, allylamine, allyl glycidyl ether, the allyl ether of piperidine, preferably the allyl ether of sterically hindered piperidine, styrenes, preferably α-methylstyrene, 1,2-epoxy-4-vinylcyclohexane, allyl chloride, chlorinated alkenes, preferably allyl chloride, and fluorinated alkenes, preferably 4,4,5,5,6,6,7,7,7-nonafluoro-1-heptene.

The unsaturated compound can also be chosen from compounds comprising several alkene functional groups, preferably two or three alkene functional groups, and particularly preferably be chosen from the following compounds:

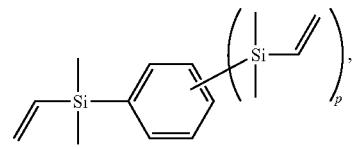

with p having the value 1 or 2,

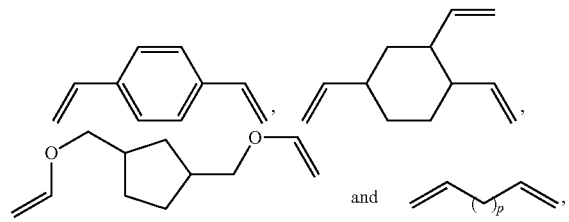

with q having a value from 2 to 6, preferably q having the value 2 or 4.

The unsaturated compound can also be chosen from polyorganosiloxane (currently denoted POS) compounds comprising units of formula (X):

$$A_g U_h SiO_{(4-(g+h))/2} \qquad (X)$$

in which:
  the A radicals, which are identical or different, represent a linear or branched alkenyl or alkynyl radical containing between 2 and 6 carbon atoms;
  the U radicals, which are identical or different, represent a monovalent radical other than a hydrogen atom,
  g and h represent integers, g having the value 1 or 2, h having the value 0, 1 or 2 and (g+h) having the value 1, 2 or 3;
  and optionally comprising other units of formula (XI):

$$U_i SiO_{(4-i)/2} \qquad (XI)$$

in which U has the same meaning as above and i represents an integer of between 0 and 3.

In the formula (X) and in the formula (XI), U can represent a monovalent radical chosen from the group consisting of an alkyl group having from 1 to 8 carbon atoms, optionally substituted by at least one halogen atom, and an aryl group. U can advantageously represent a monovalent radical chosen from the group consisting of methyl, ethyl, propyl, 3,3,3-trifluoropropyl, xylyl, tolyl and phenyl.

Examples of polyorganosiloxanes which can be unsaturated compounds are:
  a poly(dimethylsiloxane) having dimethylvinylsilyl ends;
  a poly(dimethylsiloxane-co-methylphenylsiloxane) having dimethylvinylsilyl ends;
  a poly(dimethylsiloxane-co-methylvinylsiloxane) having dimethylvinylsilyl ends;
  a poly(dimethylsiloxane-co-methylvinylsiloxane) having trimethylsilyl ends;
  and
  a cyclic poly(methylvinylsiloxane).

According to a specific embodiment of the present invention, it is possible for the unsaturated compound, comprising at least one alkene functional group and/or at least one alkyne functional group, and the compound comprising at least one hydrosilyl functional group to be one and the same compound, comprising, on the one hand, at least one alkene functional group and/or at least one alkyne functional group and, on the other hand, at least one silicon atom and at least one hydrogen atom bonded to the silicon atom. This compound can then be described as "bifunctional", and it is capable of reacting with itself by a hydrosilylation reaction. The invention can thus also relate to a process for the hydrosilylation of a bifunctional compound with itself, said bifunctional compound comprising, on the one hand, at least one alkene functional group and/or at least one alkyne functional group, and, on the other hand, at least one silicon atom and at least one hydrogen atom bonded to the silicon atom, said process being characterized in that it is catalyzed by a metal complex as described above.

Examples of polyorganosiloxanes which can be bifunctional compounds are:
- a poly(dimethylsiloxane-co-hydromethylsiloxane-co-vinylmethylsiloxane) having dimethylvinylsilyl ends;
- a poly(dimethylsiloxane-co-hydromethylsiloxane-co-vinylmethylsiloxane) having dimethylhydrosilyl ends; and
- a poly(dimethylsiloxane-co-hydromethylsiloxane-co-propyl glycidyl ether methylsiloxane) having trimethylsilyl ends.

In that which follows, when the use of the unsaturated compound and of the compound comprising at least one hydrosilyl functional group is concerned, a person skilled in the art will understand that this is also understood to mean the use of a bifunctional compound.

The hydrosilylation reaction can be carried out in a solvent or in the absence of solvent. In an alternative form, one of the reactors, for example the unsaturated compound, can act as solvent. Appropriate solvents are solvents which are miscible with the compound comprising at least one hydrosilyl functional group.

The hydrosilylation reaction can be carried out at a temperature of between 15° C. and 300° C., preferably between 20° C. and 240° C., more preferably between 70° C. and 200° C., more preferably between 50° C. and 140° C. and even more preferably between 50° C. and 100° C.

Another subject matter of the present invention is a means especially designed for the implementation of the hydrosilylation process described above. This means consists of a composition comprising:
- at least one unsaturated compound comprising at least one alkene functional group and/or at least one alkyne functional group,
- at least one compound comprising at least one hydrosilyl ($\equiv$Si—H) functional group, and
- a catalyst chosen from the metal complexes as described above.

This composition forms the reaction medium in which the hydrosilylation reaction according to the invention can take place. In order to do this, this composition can be heated, as described above.

The relative amounts of unsaturated compound and of compound comprising at least one hydrosilyl functional group can be controlled so as to ensure a degree of reaction of the unsaturations with hydrosilyl functional groups. The molar ratio of the Si—H functional groups of the compounds comprising at least one hydrosilyl functional group to the alkene and alkyne functional groups of the unsaturated compounds is preferably between 1:100 and 100:1 and more preferably between 1:10 and 10:1. According to one embodiment, the molar ratio of the Si—H functional groups of the compounds comprising at least one hydrosilyl functional group to the alkene and alkyne functional groups of the unsaturated compounds is strictly less than 1. The Si—H functional groups are in this instance in deficit with respect to the unsaturated functional groups. According to another embodiment, the molar ratio of the Si—H functional groups of the compounds comprising at least one hydrosilyl functional group to the alkene and alkyne functional groups of the unsaturated compounds is strictly greater than 1. The Si—H functional groups are then in excess with respect to the unsaturated functional groups.

According to the invention, the hydrosilylation reaction is carried out in the presence of a catalytic amount of one or more metal complexes having a silene ligand. The term "catalytic amount" is understood to mean less than a molar equivalent of metal, with respect to the amount of unsaturations present in the reaction medium. The concentration of catalyst in the composition according to the invention can typically be between 5 ppm and 10 ppm by weight, with respect to the unsaturated reactant. However, entirely advantageously, the inventors have discovered that particularly low contents of catalyst according to the invention are sufficient in order to obtain a high degree of conversion and a high hydrosilylation yield. This is why the concentration of catalyst in the composition according to the invention can very advantageously be less than 10 ppm by weight, more preferably less than 5 ppm by weight, more preferably between 0.1 ppm and 3 ppm by weight and even more preferably between 0.1 ppm and 1 ppm by weight, with respect to the weight of the unsaturated reactant.

In addition to the unsaturated compound comprising at least one alkene functional group and/or at least one alkyne functional group and the compound comprising at least one hydrosilyl functional group, this composition can optionally comprise additives.

According to one embodiment of the invention, an inhibitor or retarder of the hydrosilylation reaction can be added to the composition according to the invention. These compounds are known to a person skilled in the art and are available commercially. Mention may be made, for example, of the following compounds: polyorganosiloxanes substituted by at least one alkenyl which can optionally be provided in a cyclic form, tetramethylvinyltetrasiloxane being particularly preferred; pyridine; organic phosphines and phosphites; unsaturated amides; alkyl maleates; and acetylenic alcohols.

Acetylenic alcohols (for example described in the patent documents FR 1 528 464 and FR 2 372 874), which are among the preferred hydrosilylation reaction thermal blockers, have the formula:

(R')(R")C(OH)—C≡CH in which formula R' is a linear or branched alkyl radical or a phenyl radical and R" is a hydrogen atom, a linear or branched alkyl radical or a phenyl radical, it optionally being possible for the R', R" radicals and the carbon atom located in the a position with respect to the triple bond to form a ring, the total number of carbon atoms present in R' and R" being at least 5 and preferably from 9 to 20.

Mention may be made, for said acetylenic alcohols, by way of example, of:
- 1-ethynylcyclohexan-1-ol;
- 3-methyldodec-1-yn-3-ol;
- 3,7,11-trimethyldodec-1-yn-3-ol;

1,1-diphenylprop-2-yn-1-ol;
3-ethyl-6-ethylnon-1-yn-3-ol;
2-methylbut-3-yn-2-ol;
3-methylpentadec-1-yn-3-ol; and
diallyl maleate or diallylmaleate derivatives.

The compositions of the invention can additionally comprise normal functional additives. Mention may be made, as families of normal functional additives, of:
fillers;
adhesion promoters;
adhesion modifiers;
additives for stability towards heat;
additives for enhancing the consistency;
pigments;
additives for stability towards heat, for stability towards oil or for stability towards fire, for example metal oxides.

The fillers optionally provided are preferably inorganic. They can in particular be siliceous fillers. As regards siliceous materials, they can act as reinforcing or semireinforcing filler. Reinforcing siliceous fillers are chosen from colloidal silicas, fumed or precipitated silica powders or their mixtures. These powders exhibit a mean particle size generally of less than 0.1 μm (micrometers) and a BET specific surface of greater than 30 $m^2/g$, preferably of between 30 and 350 $m^2/g$. Semireinforcing siliceous fillers, such as diatomaceous earths or ground quartz, can also be employed. As regards nonsiliceous inorganic materials, they can be involved as semireinforcing or bulking inorganic filler. Examples of these nonsiliceous fillers, which can be used alone or as a mixture, are carbon black, titanium dioxide, aluminum oxide, aluminum hydrate, expanded vermiculite, unexpanded vermiculite, calcium carbonate, optionally surface-treated with fatty acids, zinc oxide, mica, talc, iron oxide, barium sulfate and slaked lime. These fillers have a particle size distribution generally between 0.001 and 300 μm (micrometers) and a BET specific surface of less than 100 $m^2/g$. In practice but nonlimitingly, the fillers employed can be a mixture of quartz and silica. The fillers can be treated with any appropriate product. With regard to weight, it is preferable to employ an amount of filler of between 1% and 50% by weight, preferably between 1% and 40% by weight, with respect to all of the constituents of the composition.

More generally, quantitatively, the compositions according to the invention can exhibit proportions which are standard in the technical field under consideration, it being known that the target application also has to be taken into account.

Apart from the hydrosilylation, the metal complex can also be used according to the present invention as catalyst for coupling reactions, in particular the reactions chosen from the group consisting of: the Heck reaction, the Suzuki reaction, aryl halide amination, amide α-arylation, the Sonogashira coupling, the Kumada coupling, the Stille reaction and alkyne coupling reactions. For the record, the Heck reaction is a coupling between an unsaturated halogenated derivative, in particular an aryl halide or an unsaturated triflate, and an alkene; the Suzuki reaction is a coupling between two aryl groups, in particular between a boronic acid and a halogenated derivative; the Sonogashira coupling is a direct coupling reaction between an aryl or vinyl halide and a terminal alkyne; the Kumada coupling is a cross coupling reaction between an alkyl or aryl Grignard reagent and an aryl or vinyl halide; the Stille reaction is a coupling between an organotin compound and a halide. Alkyne coupling reactions are particularly useful for furan synthesis.

Furthermore, the metal complex can also be used according to the present invention as catalyst for olefin metathesis reactions. The metathesis of olefins consists of the cleaving of the double bond of an alkene, followed by the redistribution of the alkylidene fragments formed. Mention may be made, among reactions employing the metathesis of olefins, of:
polymerization reactions, for example ring-opening metathesis polymerization (ROMP) and acyclic diene metathesis (ADMET) polymerization;
intermolecular coupling reactions, for example ring-closing metathesis (RCM);
intermolecular coupling reactions, for example cross metathesis (CM) coupling.

The metal complex can also be used according to the present invention as catalyst for polymerization reactions, for example the copolymerization of ethylene and carbon monoxide in order to form polyketones and atom transfer radical polymerization (ATRP), as catalyst for the hydrogenation and hydroformylation of alkenes and arenes, as catalyst for the dehalogenation of aryl halides, as catalyst for the cyclopropanation of olefins with a diazoalkane, or as catalyst for the arylation and alkenylation of aldehydes, in particular by boronic acid derivatives.

Another subject matter of the present invention is any one of the abovementioned reactions, characterized in that it is catalyzed by a metal complex as described above.

The use of the metal complexes according to the invention as catalysts can be particularly advantageous when the reaction catalyzed is an asymmetric synthesis reaction.

Other aims, characteristics and advantages of the invention will become apparent from the following examples, which are given purely by way of illustration and without limitation.

EXAMPLES

Example 1

Synthesis of Silene-Phosphorus Ylide Ligand 1

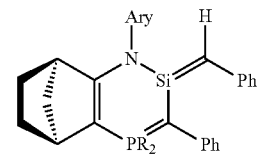

with "PR$_2$" =

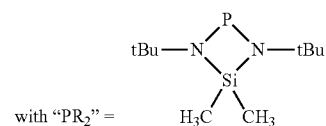

and "Ary" =

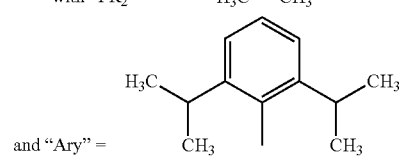

All the handling operations are carried out under an inert argon atmosphere using Schlenk glassware or high pressure NMR tubes. Dry oxygen-free solvents were employed. The $^1$H, $^{13}$C, $^{29}$Si and $^{31}$P NMR spectra were recorded on Avance 300 spectrometers. The $^1$H, $^{29}$Si and $^{13}$C NMR chemical shifts are given in ppm with respect to an SiMe$_4$ internal standard. The $^{31}$P NMR chemical shifts are expressed in ppm with respect to 85% H$_3$PO$_4$.

Stage 1: Synthesis of the Chlorophosphine (a)

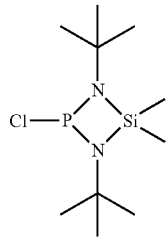

151.3 ml (242.08 mmol) of n-BuLi (1.6M) were added to a solution of Me$_2$Si(NHt-Bu)$_2$ (24.50 g; 121.04 mmol) in 80 ml of toluene at −78° C. After returning to ambient temperature, the solution was heated at 50° C. for 4 h. A solution of PCl$_3$ (11.7 ml; 133.14 mmol) in 30 ml of toluene was cooled to −110° C. and the preceding solution was added dropwise without ever rising above −100° C. The solution was allowed to return to ambient temperature overnight. The solvent was evaporated under vacuum and the residue was taken up with 150 ml of pentane. Filtration was carried out and the chlorophosphine (a) was extracted with two times 100 ml of pentane. The pentane was evaporated under vacuum and purification was carried out by distillation under vacuum in order to obtain a colorless oil (18.27 g; Yield: 56.6%).

Stage 2: Synthesis of the Imine (b)

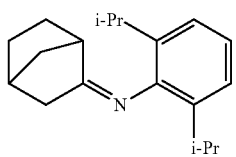

2,6-Diisopropylaniline (85.3 ml; 481.34 mmol) and a catalytic amount of para-toluenesulfonic acid were added to a solution of norcamphor (53.02 g; 481.34 mmol) in 200 ml of toluene. The mixture was heated at 135° C. with a Dean Stark apparatus for 72 h. The solvent was evaporated and the solid was taken up in pentane. The solution was subsequently concentrated and subjected to crystallization at −30° C. overnight. The imine (b) was obtained in the form of slightly brown crystals (119.22 g; Yield: 92.0%).

Stage 3: Synthesis of the Iminophosphine (c)

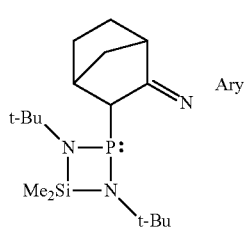

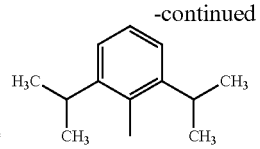

44.9 ml (71.79 mmol) of n-BuLi (1.6M) were added to a solution of the imine (b) (18.40 g; 68.38 mmol) in 150 ml of THF at −78° C. and the mixture was allowed to return to ambient temperature. After stirring for 1 h, the solution was again cooled to −78° C. and the chlorophosphine (a) (18.23 g; 68.38 mmol) was added. The mixture was allowed to return to ambient temperature and the solvent was evaporated under vacuum. The solid was taken up with 120 ml of pentane and filtration was carried out. Extraction was carried out with three times 50 ml of pentane. The product was subsequently purified by washing it with three times 40 ml of acetonitrile in order to obtain a white solid (24.25 g; Yield: 71.0%).

Stage 4: Synthesis of the phosphino-N-silylenamine (d)

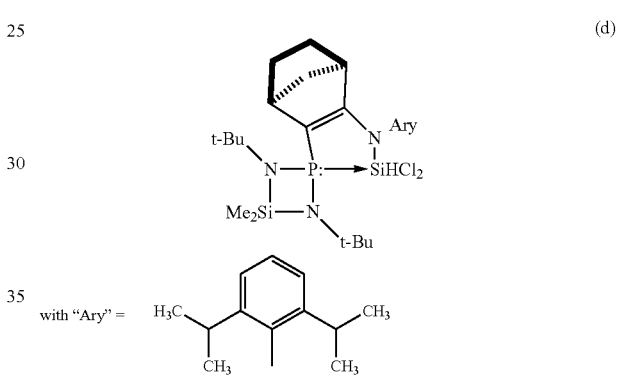

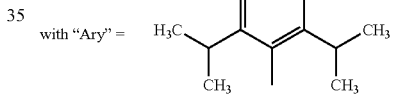

9.8 ml (15.71 mmol) of n-BuLi (1.6M) were added to a solution of iminophosphine (c) (7.85 g; 15.71 mmol) in 80 ml of THF at −78° C. and the mixture was allowed to return to ambient temperature. After stirring for 1 h, the solution was again cooled to −78° C. and one equivalent of SiHCl$_3$ (1.6 ml; 15.71 mmol) was added. The mixture was allowed to return to ambient temperature with stirring for 1 h and then the solvent was evaporated under vacuum. The solid was taken up with 60 ml of pentane and filtration was carried out.

Extraction was carried out with two times 40 ml of diethyl ether. The solution was concentrated and submitted to crystallization at −30° C. Pale yellow crystals are obtained (7.81 g; Yield: 83.0%).

Stage 5: Synthesis of the Hydrosilylene (e)

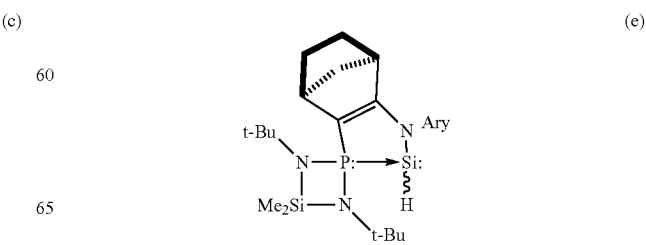

with "Ary" = 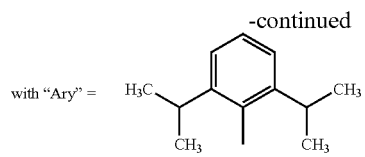

Magnesium powder (130 mg; 5.35 mmol) was added to a solution of the compound (d) (2.46 g; 4.10 mmol) in 80 ml of THF. After stirring overnight at ambient temperature, the solvent was evaporated under vacuum and the residue was taken up with 40 ml of pentane. The solution was filtered and the silylene (e) was extracted with two times 40 ml of pentane. After evaporation of the solvent, the residue was washed with two times 3 ml of cold pentane in order to obtain the analytically pure silylene (e) in the form of a pale yellow solid (1.52 g; Yield: 70.2%).

Stage 6: Synthesis of the Silylene (f)

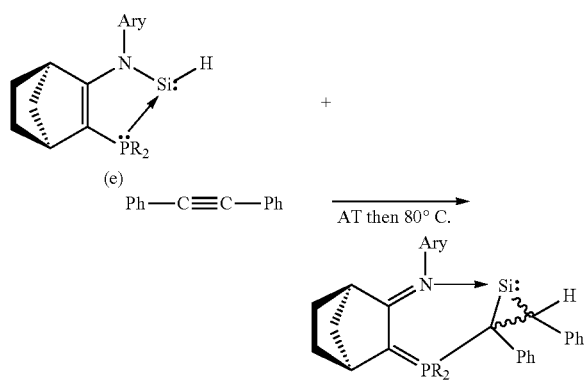

Diphenylacetylene (1.58 mmol) was added to a solution of the compound (e) (0.83 g, 1.58 mmol) in toluene (5 ml) at ambient temperature. The solution was heated to 80° C. After 15 hours at 80° C., all the volatile compounds were removed under vacuum. After washing the residue with pentane (7 ml), the silylene compound (f) was obtained in the form of a white solid (0.96 g, 81%).

Stage 7: Synthesis of the Silene-Phosphorus Ylide 1

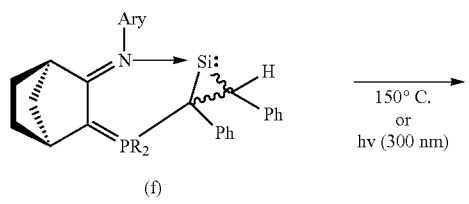

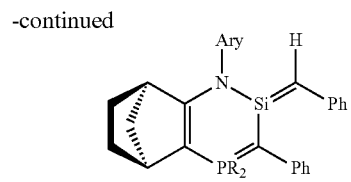

with "PR₂" = 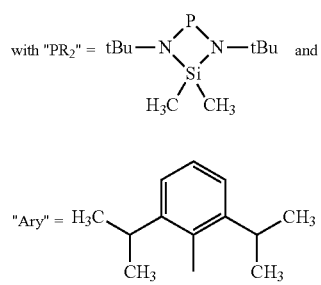 and

"Ary" = H₃C (structure shown)

A high-pressure NMR tube containing a solution of (f) (50.3 mg, 0.071 mmol) in toluene was subjected to 3 bar of $N_2$ and heated at 150° C. for 8 hours or else irradiated (hν=300 nm) at ambient temperature for 4 hours. All the volatile compounds were removed under vacuum. After addition of dry pentane (0.6 ml) to the residue, the analytically pure compound 1 was obtained in the form of orange crystals (38.3 mg, 76%). Crystals suitable for an X-ray diffraction analysis were obtained by crystallization from a pentane solution.

Characterization of the product 1:

Melting point: 194-195° C.

$^1$H NMR (300.18 MHz, $C_6D_6$, 25° C.): δ=0.08 (s, 3H, $CH_{3Si}$), 0.16 (s, 3H, $CH_{3Si}$), 0.79 (s, 9H, 3×$CH_{3tBu}$), 0.78 (overlapped, 1H, ½ $CH_{2Norb}$), 1.02 (d, $J_{HH}$=6.9 Hz, 3H, $CH_{3iPr}$), 1.04 (d, $J_{PH}$=0.5 Hz, 9H, 3×$CH_{3tBu}$), 1.07 (d, $J_{HH}$=6.9 Hz, 3H, $CH_{3iPr}$), 1.17 (m, 2H, ½ $CH_{2CbridgeheadCP}$), 1.25 (d, $J_{HH}$=6.8 Hz, 3H, $CH_{3iPr}$), 1.30-1.52 (m, 3H, $CH_{2CbridgeheadCN}$, ½ $CH_{2Norb}$), 1.43 (d, $J_{HH}$=6.8 Hz, 3H, $CH_{3iPr}$), 2.29 (br s, 1H, PCCH$_{bridgehead}$), 2.91 (br s, 1H, NCCH$_{bridgehead}$), 3.15 (m, $^2$H, $CH_{iPr}$, SiCH), 3.25 (sep, $J_{HH}$=6.8 Hz, 1H, $CH_{iPr}$), 6.25-7.11 (11H, $H_{Ar}$), 7.46 ppm (d, $J_{HH}$=7.9 Hz, 2H, $H_{Ar}$).

$^{13}$C{$^1$H} NMR (75.47 MHz, $C_6D_6$, 25° C.): δ=3.6 (d, $J_{PC}$=2.3 Hz, $CH_{3Si}$), 4.5 (d, $J_{PC}$=1.8 Hz, $CH_{3Si}$), 24.0 (s, $CH_{3iPr}$), 24.3 (s, $CH_{3iPr}$), 25.5 (s, $CH_{3iPr}$), 25.9 (d, $J_{PC}$=2.3 Hz, $CH_{2CbridgeheadCP}$), 26.0 (s, $CH_{3iPr}$), 27.6 (s, $CH_{2CbridgeheadCN}$), 28.7 (s, $CH_{iPr}$), 29.0 (s, $CH_{iPr}$), 31.7 (d, $J_{PC}$=5.4 Hz, 3C, 3×$CH_{3tBu}$), 32.2 (d, $J_{PC}$=5.4 Hz, 3C, 3×$CH_{3tBu}$), 43.8 (d, $J_{PC}$=8.4 Hz, NCCH$_{bridgehead}$), 45.4 (d, $J_{PC}$=11.1 Hz, PCCH$_{bridgehead}$), 47.9 (d, $J_{PC}$=6.5 Hz, $CH_{2Norb}$), 52.2 (s, $C_{tBu}$), 52.5 (s, $C_{tBu}$), 54.5 (d, $J_{PC}$=100.6 Hz, PCSi), 60.9 (br d, $J_{PC}$=6.1 Hz, SiCH), 98.6 (d, $J_{PC}$=125.8 Hz, PC=CN), 117.9 (s, $CH_{Ar}$), 123.3 (d, $J_{PC}$=1.6 Hz, $CH_{Ar}$), 125.9 (s, 2×$CH_{Ar}$), 127.4 (s, 2×$CH_{Ar}$), 128.6 (s, $CH_{Ar}$), 128.7 (s, 2×$CH_{Ar}$), 130.9 (s, $CH_{Ar}$), 131.0 (s, $CH_{Ar}$), 137.5 (s, $C_{Ar}$), 139.9 (d, $J_{PC}$=2.6 Hz, $C_{Ar}$), 145.5 (s, $C_{Ar}$), 146.6 (s, $C_{Ar}$), 147.3 (s, $C_{Ar}$), 167.2 ppm (d, $J_{PC}$=8.7 Hz, PC=CN).

$^{29}$Si{$^1$H} NMR (59.63 MHz, $C_6D_6$, 25° C.): δ=3.3 (s, $Si_{Me}$), 74.7 ppm (d, $J_{PSi}$=24.0 Hz, $Si_{CP}$).

$^{31}$P{$^1$H} NMR (121.49 MHz, $C_6D_6$, 25° C.): δ=27.4 ppm (s).

Example 2

Synthesis of the Metal Complex Having a Silene-Phosphorus Ylide Ligand 2

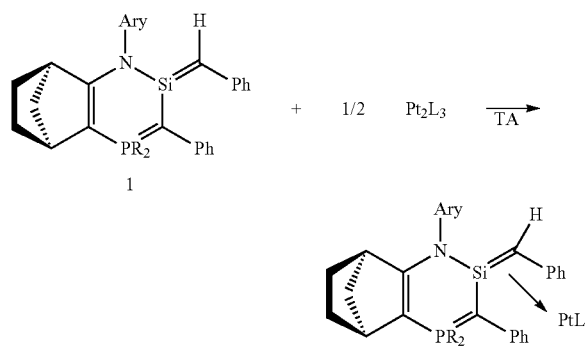

A solution of platinum(0)(1,3-divinyl-1,1,3,3-tetramethyldisiloxane) complex in xylene (0.91 M) was added at ambient temperature to a round-bottomed flask containing the product 1 (45 mg; 0.064 mmol). All the volatile compounds were subsequently removed under vacuum and the solid was washed with pentane in order to give the analytically pure product 2 in the form of yellow crystals (19.9 mg, 31%). Crystals of the product 2 suitable for X-ray diffraction analysis were obtained by crystallization from a pentane solution at −50° C.

The metal complex 2 thus obtained is stable under argon.

Characterization of the product 2:

Melting point: 204-205° C.

$^1$H NMR (300.18 MHz, CDCl$_3$, 25° C.): δ=−0.79 (s, 3H, CH$_{3Si}$), −0.18 (s, 3H, CH$_{3Si}$), −0.09 (s, 3H, CH$_{3Si}$), 0.31 (s, 3H, CH$_{3Si}$), 0.36 (s, 3H, CH$_{3Si}$), 0.50 (s, 3H, CH$_{3Si}$), 0.73 (d, J$_{HH}$=7.0 Hz, $^3$H, CH$_{3iPr}$), 0.96-1.05 (m, 9H, 3×CH$_{3iPr}$), 1.05 (m, 2H, CH$_{2cbridgeheadCP}$), 1.18 (s, 9H, 3×CH$_{3tBu}$), 1.09 (br, 1H, ½ CH$_{2Norb}$), 1.36 (d, J$_{PH}$=0.5 Hz, 9H, 3×CH$_{3tBu}$), 1.53 (br, 1H, ½ CH$_{2Norb}$), 1.68 (m, 2H, CH$_{2CbridgeheadCN}$), 1.84 (br, 1H, Si—CH=CH$_2$), 2.22 (br, 1H, ½ Si—CH=CH$_2$), 2.42 (br s, 1H, PCCH$_{bridgehead}$), 2.71 (sep, J$_{HH}$=10.5 Hz, 1H, CH$_{iPr}$), 2.82 (br, 1H, ½ Si—CH=CH$_2$), 3.15 (br s, 1H, NCCH$_{bridgehead}$), 3.24 (br, 1H, ½ Si—CH=CH$_2$), 3.25 (br, 1H, ½ Si—CH=CH$_2$), 3.27 (br, 1H, Si—CH=CH$_2$), 3.44 (sep, J$_{HH}$=10.8 Hz, 1H, CH$_{iPr}$), 6.08-7.66 (13H, H$_{Ar}$), $^{13}$C{1H} NMR (75.47 MHz, CDCl$_3$, −50° C.): δ=−2.91 (br s, CH$_{3Si}$), −1.35 (br s, CH$_{3Si}$), 1.20 (br s, CH$_{3Si}$), 2.65 (br s, CH$_{3Si}$), 4.24 (s, CH$_{3Si}$), 4.80 (br s, CH$_{3Si}$), 23.5 (s, CH$_{3iPr}$), 24.9 (s, CH$_{3iPr}$), 25.4 (br, CH$_{2CbridgeheadCP}$), 25.8 (s, CH$_{3iPr}$), 26.3 (s, CH$_{3iPr}$), 27.5 (s, CH$_{2CbridgeheadCN}$), 27.8 (s, CH$_{iPr}$), 28.0 (s, 31.7 (d, J$_{PC}$=4.5 Hz, 3C, 3×CH$_{3tBu}$), 32.8 (d, J$_{PC}$=4.3 Hz, 3×CH$_{3tBu}$), 38.6 (d, J$_{PC}$=106.0 Hz, PCSi), 42.9 (d, J$_{PC}$=9.8 Hz, NCCH$_{bridgehead}$), 44.5 (s, Si—CH=CH$_2$), 46.1 (d, J$_{PC}$=10.5 Hz, PCCH$_{bridgehead}$), 47.3 (d, J$_{PC}$=2.6 Hz, CH$_{2Norb}$), 51.5 (s, CtBu), 52.3 (s, CtBu), 56.7 (s, Si—CH=CH$_2$), 66.3 (s, Si—CH=CH$_2$), 79.9 (s, Si—CH=CH$_2$), 98.4 (d, J$_{PC}$=125.0 Hz, PC=CN), 119.8 (s, CH$_{Ar}$), 121.3 (s, CH$_{Ar}$), 123.8 (s, 2×CH$_{Ar}$), 124.6 (s, CH$_{Ar}$), 126.5 (s, CH$_{Ar}$), 127.3 (s, 2×CH$_{Ar}$), 127.5 (s, CH$_{Ar}$), 129.8 (s, CH$_{Ar}$), 129.9 (s, CH$_{Ar}$), 130.2 (s, CH$_{Ar}$), 132.3 (s, CH$_{Ar}$), 138.4 (s, C$_{Ar}$), 143.1 (s, C$_{Ar}$), 146.8 (s, C$_{Ar}$), 147.9 (s, C$_{Ar}$), 148.8 (s, C$_{Ar}$), 167.3 ppm (d, Jp$_c$=9.2 Hz, PC=CN), $^{29}$Si{1H} NMR (59.63 MHz, CDCl$_3$, −50° C.): δ=0.7 (s, Si$_{Me}$), 3.7 (s, Si$_{Me}$), 6.7 ppm (s, Si$_{Me}$), $^{31}$P{1H} NMR (121.49 MHz, CDCl$_3$, 25° C.): δ=24.9 ppm (J$_{PPt}$=21.0 Hz).

Example 3

Hydrosilylation of 1-Octene with Bis(Trimethylsiloxy)Methylhydrosilane Catalyzed by a Platinum Complex Having a Silylene Ligand

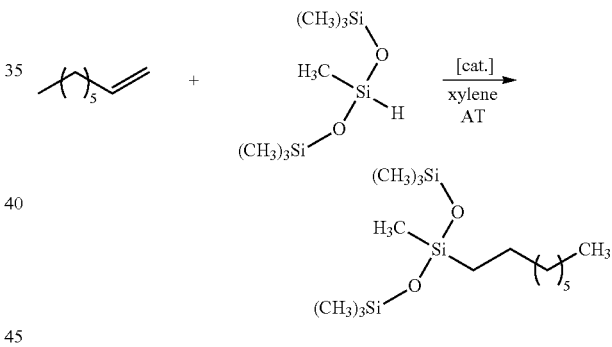

In this example, the product 2 obtained in example 2 was used as catalyst.

Solutions containing different concentrations of product 2 in xylene were prepared: a 0.09 M solution was obtained by dissolving 51 mg (0.046 mmol) of the product 2 in 0.5 ml of xylene. 0.009 M and 0.0009 M solutions were prepared from the first solution by diluting 0.1 ml of the first solution in 1 ml and 10 ml respectively.

1 μl of solution of catalyst 2 in xylene was added at ambient temperature to a solution of 1-octene (1.85 mmol) and bis(trimethylsiloxy)methylhydrosilane (1.85 mmol) in xylene (1 ml). The combination was heated with stirring at 72° C. and then deactivated by exposing the reaction mixture to air. At the end of the reaction, all the volatile compounds were removed under vacuum and the analytically pure product was obtained in the form of a colorless liquid.

On conclusion of the reaction, the degree of conversion of the reactants and the yield were determined by gas chromatography.

Several tests were carried out while varying the concentration of catalyst. In addition, comparative tests were carried out using the Karstedt platinum complex (Pt$_2$(DVT MS)$_3$) as catalyst. The results are given in table 1:

TABLE 1

| Test | Catalyst | Concentration of catalyst | | | Duration of the reaction | Degree of conversion | Yield |
|---|---|---|---|---|---|---|---|
| | | ppm | mol % | weight % | | | |
| 1 | Product 2 | 30 | $3 \times 10^{-3}$ | $2.8 \times 10^{-2}$ | 20 min | >95% | 96% |
| 2 | Karstedt | 3 | $3 \times 10^{-4}$ | $2.8 \times 10^{-3}$ | 4 h | >95% | 91% |
| 3 | Product 2 | 3 | | $2.5 \times 10^{-3}$ | 1 h | >95% | 91% |
| 4 | Karstedt | 0.3 | $3 \times 10^{-5}$ | $2.8 \times 10^{-4}$ | 24 h | 50% | 48% |
| 5 | Product 2 | | | $2.5 \times 10^{-4}$ | 14 h | 95% | 90% |

The concentrations of the catalyst in mol % and in weight % are expressed with respect to the 1-octene.

It was found that high degrees of hydrosilylation conversion were obtained using the product 2 as catalyst, even with very low concentrations, of the order of $2.5 \times 10^{-4}$ weight %. In comparison with the Karstedt catalyst, the platinum complex having a silene ligand made it possible to obtain higher degrees of conversion when very low contents of catalyst were used.

Furthermore, on comparing the degree of conversion obtained with the yield, it is found that the isomerization of the 1-octene is very limited.

Example 4

Hydrosilylation of 1-Octene with Triethylhydrosilane Catalyzed by a Platinum Complex Having a Silene-Phosphorus Ylide Ligand

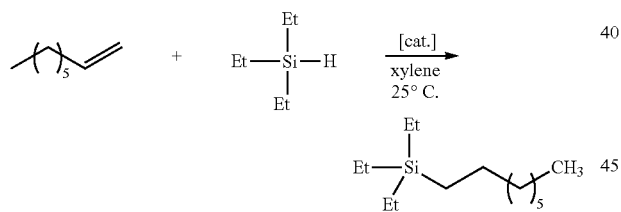

In this example, the product 2 obtained in example 2 was used as catalyst. Solutions of different concentrations of catalyst 2 in xylene were prepared as in example 3.

10.0 µl of solution of catalyst 2 in xylene were added at ambient temperature to a solution of 1-octene (2.00 mmol) and triethylhydrosilane (2.00 mmol) in xylene (1 ml). The combination was stirred at 25° C. and then deactivated by exposing the reaction mixture to air. At the end of the reaction, all the volatile compounds were removed under vacuum and the analytically pure product was obtained in the form of a colorless liquid.

On conclusion of the reaction, the degree of conversion of the reactants and the yield were determined by gas chromatography.

Several tests were carried out while varying the concentration of catalyst. In addition, comparative tests were carried out using the Karstedt platinum complex (Pt$_2$(DVT MS)$_3$) as catalyst. The results are given in table 2:

TABLE 2

| Test | Catalyst | Concentration of catalyst | | | Duration of the reaction | Degree of conversion | Yield |
|---|---|---|---|---|---|---|---|
| | | ppm | mol % | weight % | | | |
| 1 | Product 2 | 300 | $3 \times 10^{-2}$ | $2.8 \times 10^{-1}$ | 2 h | 60% | 53% |
| 2 | Karstedt | 300 | $3 \times 10^{-2}$ | $2.5 \times 10^{-1}$ | 20 min | 0% | — |
| 3 | Karstedt | | | | 1 h | 3% | — |
| 5 | Karstedt | | | | 3 days | 9% | 8% |

The concentrations of catalyst in mol % and in weight % are expressed with respect to the 1-octene.

It is found that the reaction between the 1-octene and the triethylhydrosilane is catalyzed at ambient temperature by the metal complex having a silene-phosphorus ylide ligand, whereas the Karstedt catalyst exhibits a very low reactivity.

The invention claimed is:

1. A catalyst of a metal complex comprising at least one metal atom chosen from the metals from the group consisting of Pt, Pd, Ni, Rh, Ru, Os and Ir, wherein at least one ligand comprises a silene structure which is a silene-phosphorus ylide.

2. The catalyst of the metal complex as claimed in claim 1, wherein said ligand comprising a silene structure is the compound of formula (VI):

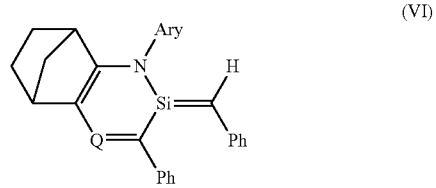

(VI)

in which the symbol "Q" represents

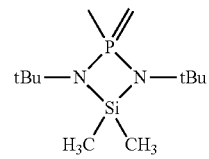

and the symbol "Ary" represents

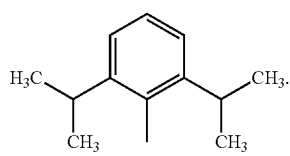

3. The catalyst of the metal complex claimed in claim 1, wherein the metal complex is the compound of formula (VII):

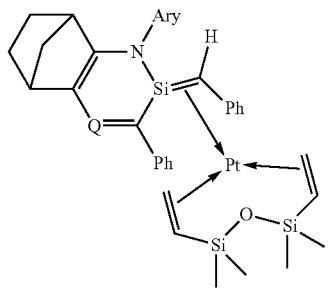

in which the symbol "Q" represents

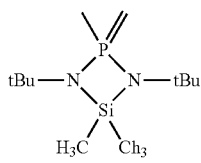

and
the symbol "Ary" represents

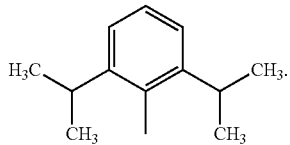

4. The catalyst of the metal complex claimed claim 1, wherein the metal complex is used as catalyst for a hydrosilylation reaction.

5. A process for the hydrosilylation of an unsaturated compound comprising at least one alkene functional group and/or at least one alkyne functional group with a compound comprising at least one hydrosilyl functional group, said process is catalyzed by a metal complex comprising at least one metal atom chosen from the metals from the group consisting of Pt, Pd, Ni, Rh, Ru, Os and Ir, wherein at least one ligand comprises a silene structure which is a silene-phosphorus ylide.

6. The process as claimed in claim 5, in which the compound comprising at least one hydrosilyl functional group is chosen from the group consisting of:
   a silane or polysilane compound comprising at least one hydrogen atom bonded to a silicon atom;
   a siloxane compound comprising at least one hydrogen atom bonded to a silicon atom comprising, per molecule, at least two hydrosilyl functional groups;
   an organic polymer comprising hydrosilyl functional groups at the terminal positions.

7. A composition comprising:
   at least one unsaturated compound comprising at least one alkene functional group and/or at least one alkyne functional group,
   at least one compound comprising at least one hydrosilyl functional group, and
   a catalyst chosen from the metal complexes comprising at least one metal atom chosen from the metals from the group consisting of Pt, Pd, Ni, Rh, Ru, Os and Ir, wherein at least one ligand comprises a silene structure which is a silene-phosphorus ylide.

8. The composition as claimed in claim 7, wherein the concentration of catalyst in the composition is less than 10 ppm by weight, with respect to the weight of unsaturated reactant.

9. A metal complex comprising at least one metal atom chosen from the metals from the group consisting of Pt, Pd, Ni, Rh, Ru, Os and Ir, wherein at least one ligand comprises a silene-phosphorus ylide structure.

* * * * *